United States Patent [19]

Rodicker

[11] 4,006,406
[45] Feb. 1, 1977

[54] INDUCTIVELY OPERATED SENSOR FOR TESTING TECHNOLOGICAL QUANTITIES OF A FERROMAGNETIC WORK PIECE

[75] Inventor: Joachim Rodicker, Braunschweig, Germany

[73] Assignee: Volkswagenwerk AG., Wolfsburg, Germany

[22] Filed: Feb. 18, 1975

[21] Appl. No.: 550,385

Related U.S. Application Data

[63] Continuation of Ser. No. 404,854, Oct. 10, 1973, abandoned.

[30] Foreign Application Priority Data

Oct. 26, 1973 Germany .......................... 2252465

[52] U.S. Cl. ............................................. 324/34 R
[51] Int. Cl.² ...................................... G01R 33/12
[58] Field of Search .......... 324/34 R, 34 PE, 34 H, 324/40

[56] References Cited

UNITED STATES PATENTS 1,236,066  8/1917  Dodds ................... 324/34 R
3,281,666  10/1966  Makino .................. 324/34 R

FOREIGN PATENTS OR APPLICATIONS 1,019,143  1/1953  France .................. 324/34 R
50,035  10/1965  Poland ................... 324/34 R Primary Examiner—Robert J. Corcoran
Attorney, Agent, or Firm—Ernest F. Marmorek

[57] ABSTRACT

An inductively operated sensor for measuring a ferromagnetic work piece. Such a sensor includes a coil arrangement which contains a core and has primary and secondary windings. The coil arrangement is disposed in a paramagnetic housing. The housing is provided with a measuring head connected to the core and intended for being pressed against the work piece. The housing is also provided with contacts for an electronic measuring unit. The electronic measuring unit includes a supply of current, an amplifier, a recorder and an evaluation unit. The measuring head has a shape which conforms exactly to the surface of the work piece, thereby to obtain reproducible measuring results.

9 Claims, 1 Drawing Figure

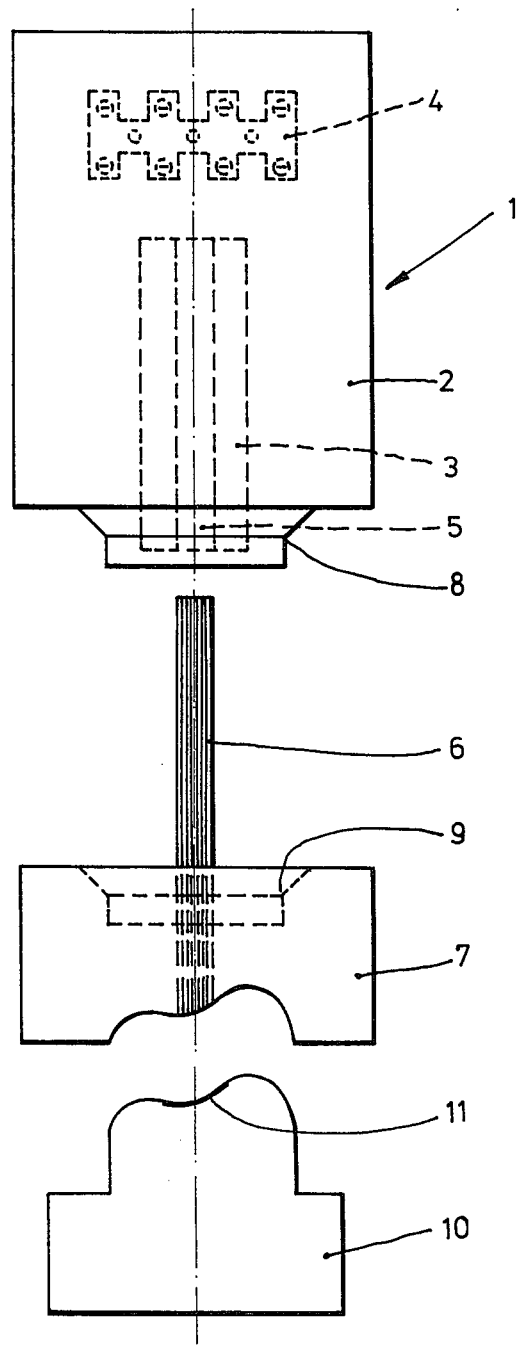

INDUCTIVELY OPERATED SENSOR FOR TESTING TECHNOLOGICAL QUANTITIES OF A FERROMAGNETIC WORK PIECE

This is a continuation of application Ser. No. 404,854, filed Oct. 10, 1973 now abandoned.

BACKGROUND OF THE INVENTION

This invention relates generally to inductively operating sensors and particularly relates to such a sensor for measuring a ferromagnetic work piece.

Such inductive sensors are utilized for the nondestructive testing of work pieces for quality control; particularly they are used for testing technologic properties such, for example, as the hardness, hardening and heat treatment of work pieces. The known sensors of the type described, however, all have the drawback that it is hardly possible to obtain exactly reproducible measuring results. There are too many influences which are hard to control and which result in a broad spread of the measuring results. Accordingly, these do not have great reliability. By way of example, it has been found that the relative position between the measuring head and the work piece during the measurements is of decisive importance for the measuring results. It is this fact which makes it practically impossible to obtain measuring values which are easily reproducible with the known sensors having spherical or ball-shaped measuring heads.

It is accordingly an object of the present invention to improve a sensor of the type described so that it is possible to obtain reliable measuring results which therefore have a higher degree of reliability and which are reproducible without difficulty.

SUMMARY OF THE INVENTION

This object is achieved in accordance with the present invention in that the measuring head is geometrically adapted to the shape of the work piece within the range to be measured. This means that the measuring head conforms closely to the outer shape of the work piece in the range to be measured. This makes it possible to provide a well-defined positioning and coupling of the sensor to the work piece which in turn will yield optimum measuring results. In accordance with a further extension of the invention it is advantageous if the measuring head with its core forms a separate unit and is detachably connected to the coil arrangement. This separation of measuring head and coil body permits a rational use of the sensor because when measuring work pieces of geometrically different shape or when measuring the same work piece but at a different region with geometrically different form, it is only necessary to exchange the measuring head with its associated core with another which conforms to the shape of the measuring range of the work piece; the housing with the coil arrangement can be utilized therefore with a plurality of measuring heads. Also, when a measuring head is damaged or has been worn off and hence is no longer usable, only the measuring head needs to be replaced and not the entire sensor. In addition the separation of measuring head and coil arrangement has the advantage that according to the testing problem and in order to obtain optimum test results (measuring sensitivity) different material for the core may be utilized. The proper selection of a suitable material for the core, which preferably is laminated, has a decisive role next to the coupling problem for the function of the sensor and the reliability of the testing results.

In case the sensor is to be used for measuring the depth of hardness of a hardened work piece it has been found to be suitable to make the core of a material containing silicon; particularly, a material which is known as dynamo sheet having a content of silicon of at least 2.5%.

On the other hand, if the sensor is to be used for measuring the surface strength of a work piece having a mechanically solidified surface, it is particularly advantageous if the core is made of a nickel-containing material. The best measuring results are obtained when the material of the core consists of a so-called transfer sheet having about 40% to about 50% nickel.

With the sensor of the invention it is possible in view of the obtainable greater measuring accuracy which is obtained by the exact coupling of the measuring head to the work piece to determined differences of structure which are somewhat deeper below the surface of the work piece. This is particularly true for the selection of a suitable material for the core if the testing of the work piece takes place with an alternating current having a frequency adapted to the depth of hardness.

In view of the fact that the particular shape of the measuring head permits a well defined positioning of the sensor at the place to be tested, the sensor of the invention may be utilized with advantage in an automatic testing machine. In this case certain technological properties of the work piece can be controlled to a large extent.

The novel features that are considered characteristic of this invention are set forth with particularity in the appended claims. The invention itself, however, both as to its organization and method of operation, as well as additional objects and advantages thereof, will best be understood from the following description when read in connection with the accompanying drawing.

BRIEF DESCRIPTION OF THE DRAWING

The single FIGURE is an exploded view of an inductively operated sensor embodying the present invention and including a work piece to be tested.

DESCRIPTION OF THE PREFERRED EMBODIMENT

As shown in the drawing the inductive sensor of the invention consists of two units; namely, the basic unit and the measuring head with core which jointly form the sensor, and the associated work piece to be tested. The electronic measuring unit which cooperates with the sensor has not been illustrated because it forms no part of the present invention.

The basic unit 1 consists of a housing 2 which is made of a paramagnetic synthetic material and in which are embedded the coil arrangement 3 and the terminals and connections 4 for the electronic measuring unit. The coil arrangement 3 is provided with an opening 5 to receive a core 6 which is preferably laminated as shown. The core 6 is solidly connected to the measuring head 7 consisting also of a paramagnetic synthetic material. For centering purposes the basic unit 1 is provided with a profile 8 and the measuring head 7 with the corresponding profile 9. In the measuring head 7 there is provided the negative shape of the contour of the work piece 10 in the region of which there is the area 11 to be tested. In this manner an exact positioning and coupling of the measuring head to the work piece 10 is possible. This in turn permits to obtain reliable and reproducible measuring results. In order to carry out the measurement the core 6 disposed at the measuring head 7 is pushed into the opening 5 of the coil arrangement 3, whereby the centering elements 8 and 9 make sure that the core is properly disposed with respect to the coil arrangement. Then the measuring head 7 is put over the work piece 10 until the end of the core 6 disposed in the measuring head touches the testing area 11 on the work piece 10. Dependent upon the state of the structure of the work piece 10 at the testing area 11 the voltage induced in the secondary winding of the coil arrangement 3 varies. This variation of the voltage which is also a measure of the state of the structure in a particular region of the work piece and thereby, for example, of the hardness or the surface stability or strength may be read by means of a electronic measuring unit which has not been illustrated. However, as explained before, this electronic measuring unit consists of a current source such as an alternating current source, an amplifier, a recorder and an evaluation unit.

What is claimed is:

1. An inductively operated sensor for the measurement of a property of a non-planar ferromagnetic workpiece, comprising
    a paramagnetic housing;
    a coil arrangement in said housing and including primary and secondary windings;
    a paramagnetic measuring head having a first side, and a second side which is provided with a measuring surface having a contour substantially matching the non-planar contour of a workpiece surface, a part of which is to be measured;
    a magnetic core mounted in said measuring head and having an endface which is exposed at said measuring surface for direct contact of said endface with said part of said workpiece surface when said measuring surface is placed into mating engagement with said workpiece surface, and an end portion projecting from said first side into operative association with said coil arrangement;
    cooperating coupling portions on said housing and first side for detachably coupling said measuring head to said housing; and
    electric terminals on said housing for connecting an electronic measuring device.

2. A sensor as defined in claim 1, wherein said core is laminated.

3. A sensor as defined in claim 1, wherein said core comprises a silicon-containing material, whereby said sensor may be utilized for measuring the depth of hardness of a hardened workpiece.

4. A sensor as defined in claim 3, wherein said core comprises silicon-containing material having a silicon content of at least 2.5%.

5. A sensor as defined in claim 1, wherein said core comprises a nickel-containing material, whereby the surface stability of a workpiece having a mechanically hardened surface may be measured.

6. A sensor as defined in claim 5, wherein said core comprises a material containing approximately 40% to approximately 50% nickel.

7. A sensor as defined in claim 1 wherein said measuring head is interchangeably mounted in said housing.

8. A method of measuring a property of a non-planar ferromagnetic workpiece, comprising the steps of
    providing a paramagnetic sensor housing which accommodates a coil arrangement and terminals for connection to an electronic measuring device;
    providing a measuring head having a side provided with a measuring surface the contour of which substantially matches the non-planar contour of a workpiece surface a part of which is to be measured, and a core which has an endface exposed at said measuring surface and an end portion that projects from another side of said measuring head;
    interchangeably connecting said measuring head with said housing so that said endportion of said core becomes located in operative relationship to said coil to form therewith a sensor;
    placing said measuring surface into mating surface-to-surface engagement with a workpiece surface so that said core endface nestingly touches said part to be measured; and
    effecting the measurement of said property while said core endface nestingly touches said part.

9. An inductively operated sensor for the measurement of a property of a ferrmagnetic workpiece having a non-planar contoured workpiece surface, comprising
    a paramagnetic housing;
    a coil arrangement in said housing and including primary and secondary windings;
    a measuring head having a first side, and a second side which is provided with a measuring surface adapted for surface-to-surface contact with said workpiece surface and having a contour substantially matching the contour of said workpiece surface a part of which is to be measured;
    a core connected to said measuring head and removably mounted in said housing so as to be replacable with a different core to adjust the measuring head to different parameters to be measured, said core having an endportion projecting from said first side into operative association with said coil arrangement;
    cooperating coupling portions on said housing and first side of said measuring head for detachably coupling said measuring head to said housing; and
    electric terminals on said housing for connecting an electronic measuring device.

* * * * *